US00PP23574P2

(12) United States Plant Patent
Bergman

(10) Patent No.: US PP23,574 P2
(45) Date of Patent: Apr. 30, 2013

(54) ***CHRYSANTHEMUM* PLANT NAMED 'CIDZ0012'**

(50) Latin Name: *Chrysanthemum×morifolium*
Varietal Denomination: CIDZ0012

(75) Inventor: Wendy R. Bergman, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 140 days.

(21) Appl. No.: 13/136,619

(22) Filed: Aug. 5, 2011

(51) Int. Cl.
*A01H 5/00* (2006.01)

(52) U.S. Cl. ..... Plt./286

(58) Field of Classification Search ..... Plt./286
See application file for complete search history.

*Primary Examiner* — Annette Para
(74) *Attorney, Agent, or Firm* — Joshua L. Price

(57) ABSTRACT

A new *Chrysanthemum* plant named 'CIDZ0012' particularly distinguished by the red-purple and white bi-colored anemone-type inflorescences, dark green foliage, uniform flowering, and an eight week flowering response.

1 Drawing Sheet

Latin name of the genus and species of the plant claimed: *Chrysanthemum×morifolium.*

Varietal denomination: 'CIDZ0012'.

BACKGROUND OF THE NEW PLANT

The present invention comprises a new *Chrysanthemum*, botanically known as *Chrysanthemum×morifolium*, and hereinafter referred to by the variety name 'CIDZ0012'.

'CIDZ0012' is a product of a planned breeding program. The new cultivar has red-purple and white bi-colored anemone-type inflorescences, dark green foliage, uniform flowering, and an eight week flowering response.

'CIDZ0012' originated from a hybridization made in February 2007 in a controlled breeding environment in Salinas, Calif., USA. The female parent was the proprietary plant designated 'Yovisalia', U.S. Plant Pat. No. 11,760, with ray floret color of about RHS 75A with disc floret color of about RHS 154A and less vigorous growth.

The male parent of 'CIDZ0012' was an unpatented, proprietary plant identified as 'YB-B1665' with light bronze inflorescences. The resultant seed was sown in July 2007 in Fort Myers, Fla., USA.

'CIDZ0012' was selected as one flowering plant within the progeny of the stated cross in December 2007 in a controlled environment in Fort Myers, Fla., USA.

The first act of asexual reproduction of 'CIDZ0012' was accomplished when vegetative cuttings were propagated from the initial selection in March 2008 in a controlled environment in Fort Myers, Fla., USA.

BRIEF SUMMARY OF INVENTION

Horticultural examination of plants grown from cuttings of the plant initiated in March 2008, and continuing thereafter, has demonstrated that the combination of characteristics as herein disclosed for 'CIDZ0012' are firmly fixed and are retained through successive generations of asexual reproduction.

'CIDZ0012' has not been observed under all possible environmental conditions. The phenotype may vary significantly with variations in environment such as temperature, light intensity and day length.

A Plant Breeder's Right for this cultivar was applied for in Canada on Aug. 17, 2010 (10-7070). 'CIDZ0012' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'CIDZ0012' with colors being as true as possible with an illustration of this type.

The photographic drawing shows in FIG. 1 four flowering potted plants of the new variety, and in FIG. 2 a close-up of the inflorescence.

DETAILED BOTANICAL DESCRIPTION

The plant descriptions, measurements, and aforementioned photographs were taken in Gilroy, Calif. in mid May 2011 under natural light. These plants were propagated and grown in Nipomo, Calif. and shipped to Gilroy, Calif. for the data collection and photographs. These plants were approximately 11 weeks of age; grown as four plants together in a six inch pot under greenhouse trial conditions.

Color references are made to The Royal Horticultural Society Colour Chart (R.H.S.) 2001.

TABLE 1

DIFFERENCES BETWEEN THE NEW VARIETY 'CIDZ0012' AND A SIMILAR VARIETY

| | 'CIDZ0012' | 'Pink Yograceland' (U.S. Plant Pat. No. 12,950) |
|---|---|---|
| Color of ray florets: | White | About RHS 75A to RHS 75B |
| Quantity of ray florets: | 17-22 | About 25 |
| Inflorescence color: | Smaller | Larger |
| Petiole color: | Green | More yellow-green |

Plant:
*Form, growth and habit*.—Herbaceous pot-type, stems upright, freely branching.
*Plant height*.—16.-18.0 cm.
*Plant height* (*inflorescence included*).—29.-33.0 cm.
*Plant width*.—17.-20.0 cm.

Roots:
*Number of days to initiate roots*.—About 4 days at about 22 degrees C.
*Number of days to produce a rooted cutting*.—About 10-12 days at 22 degrees C.
*Type*.—Fine, fibrous, free branching.
*Color*.—RHS N155B but whiter.

Foliage:
*Arrangement*.—Alternate, simple.
*Immature, leaf color, upper surface*.—RHS 139A but darker with some lighter blotching.
*Lower surface*.—RHS 147B.
*Mature, leaf color, upper surface*.—RHS 139A but darker with some lighter blotching.
*Lower surface*.—RHS 147B.
*Length*.—5.5-7.0 cm.
*Width*.—4.8-5.3 cm.
*Shape*.—Ovate.
*Base shape*.—Attenuate.
*Apex shape*.—Mucronulate.
*Margin*.—Palmately lobed; irregularly serrate.
*Texture, upper surface*.—Bifid T-shaped hairs.
*Lower surface*.—Bifid T-shaped hairs.
*Color of veins, upper surface*.—RHS N138C
*Color of veins, lower surface*.—RHS N138C.
*Petiole color*.—RHS N138C.
*Length*.—1.7-1.9 cm.
*Diameter*.—0.3 cm.
*Texture*.—Bifid T-shaped hairs.

Stem:
*Quantity of main branches per plant*.—4-6.
*Color of stem*.—RHS 138A but appears lighter due to hairs.
*Length of stems*.—15.-21.0 cm.
*Diameter*.—0.5 cm.
*Length of internodes*.—2.-3.0 cm.
*Texture*.—Bifid T-shaped hairs.
*Color of peduncle*.—RHS 138A.
*Length of peduncle*.—9.-11.0 cm.
*Peduncle diameter*.—0.2 cm.
*Texture*.—Bifid T-shaped hairs.

Inflorescence:
*Type*.—Compositae type, solitary anemone-type inflorescences, borne terminally above foliage, ray florets arranged acropetally on a capitulum.
*Quantity of short days to flowering* (*response time*).—8 weeks.
*Quantity of inflorescences per plant*.—20-30.
*Lastingness of individual blooms on the plant*.—About 4 weeks.
*Fragrance*.—Slightly spicy.

Bud (just when opening/showing color):
*Color*.—RHS N74D with hints of RHS 72C and/or RHS 77C; while some are more RHS N74D with hints of between RHS 71C and RHS 71D.
*Length*.—1.5-1.8 cm.
*Width*.—1.1-1.3 cm.
*Shape*.—Oblate.

Immature inflorescence:
*Diameter*.—3.8-4.0 cm.
*Color of ray florets, upper surface*.—Closest to RHS N155B with slight hints of color at the margins and/or apex of about RHS 186B to RHS 186C.
*Lower surface*.—Closest to RHS N155B with light overlay of RHS 186B to RHS 186C.

Mature inflorescence:
*Diameter*.—6.5-7.0 cm.
*Depth*.—2.0 cm.
*Total diameter of 'disc'*.—3.5-4.0 cm.
*Receptacle height*.—0.5 cm.
*Receptacle diameter*.—0.5-0.6 cm.

Ray florets:
*Average quantity of florets*.—17-22 in 1-2 whorls.
*Color of florets, upper surface*.—Closest to RHS N155B.
*Lower surface*.—Closest to RHS N155B with slight overlay of RHS 186B to RHS 186C and some slight RHS 70B mottled in many at the center of floret.
*Length*.—2.7-3.5 cm.
*Width*.—0.7-0.9 cm.
*Shape*.—Elliptical.
*Apex shape*.—Rounded.
*Margin*.—Entire.
*Texture, upper surface*.—Papillose.
*Lower surface*.—Papillose.

Disc florets:
*Average quantity of florets*.—Approximately 160.
*Color of florets, inside*.—Approximately RHS 71A maturing to closest to RHS N155B.
*Outside*.—Approximately RHS 71A, maturing to closest to RHS N155B with a varying overlay of shades lighter than RHS 70B; some having a slightly darker margin along the apex.
*Length*.—1.1-2.1 cm.
*Width*.—0.15-0.4 cm.
*Shape*.—Tubular, elongated.
*Apex shape*.—Acute, 5 pointed.

Phyllaries:
*Quantity*.—About 25.
*Color, upper surface*.—RHS 137B.
*Lower surface*.—RHS 137A to RHS 137B but appears lighter due to hairs.
*Length*.—0.4-0.6 cm.
*Width*.—0.2-0.3 cm.
*Shape*.—Lanceolate.
*Apex shape*.—Acute.
*Base*.—Fused.
*Margins*.—Entire; papery.
*Texture, upper surface*.—Glabrous.
*Lower surface*.—Bifid T-shaped hairs.

Reproductive organs:
*Pistil*.—1.
*Found on both florets*.—Yes.
*Length*.—0.4 cm.
*Style color*.—RHS 155C.
*Style length*.—0.35 cm.
*Stigma color*.—RHS 13B.
*Stigma shape*.—Bi-parted.
*Ovary color*.—Not observed.
*Stamens*.—4.
*Found on only disc florets*.—Yes.
*Color of filaments*.—RHS 155C but more translucent looking.
*Length filaments*.—0.15 cm.

*Anther color*.—Too dry to tell.

*Anther length*.—Less than 0.1 cm.

*Anther shape*.—Oblong.

*Color of pollen*.—Not observed.

*Pollen amount*.—Not observed.

*Fertility/seed set*.—Has not been observed on this hybrid.

*Disease/pest resistance*.—Has not been observed on this hybrid.

What is claimed is:

1. A new and distinct variety of *Chrysanthemum* plant named 'CIDZ0012' substantially as illustrated and described herein.

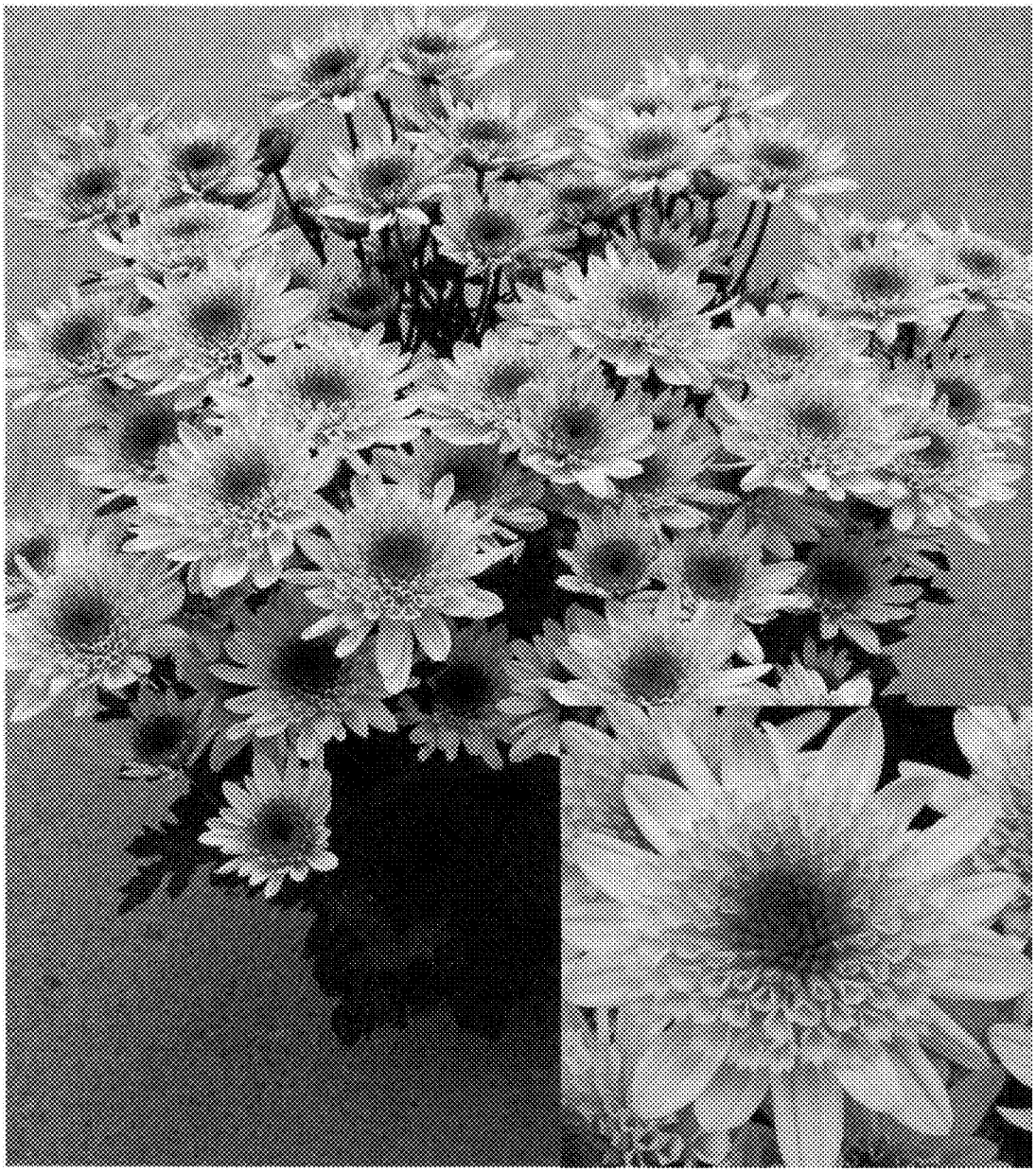

* * * * *